United States Patent
Yoshida et al.

(10) Patent No.: US 6,438,496 B1
(45) Date of Patent: Aug. 20, 2002

(54) METHOD AND APPARATUS FOR REVEALING LATENT CHARACTERISTICS EXISTING IN SYMBOLIC SEQUENCES

(75) Inventors: Tetsuhiko Yoshida, Nagoya; Kenji Oosawa, Nara; Nobuaki Obata, Nagoya, all of (JP)

(73) Assignee: Toa Gosei Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/137,162

(22) Filed: Aug. 20, 1998

(30) Foreign Application Priority Data

Aug. 20, 1997 (JP) .............................. 9-223908

(51) Int. Cl.$^7$ .......................... G01N 33/48; G06F 19/00; C12Q 1/68
(52) U.S. Cl. ................. 702/19; 435/6; 702/20
(58) Field of Search ...................... 435/6, 91.2; 702/19, 702/20

(56) References Cited

FOREIGN PATENT DOCUMENTS

EP    0 561 563    9/1993

OTHER PUBLICATIONS

Doron Witztum, et al., "Equidistant Letter Sequences In The Book Of Genesis", Statistical Science, vol. 9, No. 3, (1994), pp. 429–438.
Dear et al., Nucleic Acids Research, vol. 19, No. 14, pp. 3907–3911, 1991.*
Yoshida et al, "Color–Coding Reveals Tandem Repeats In The Escherichia Coli Genome", J. Mol. Biol. 298, 343–349 (2000).
Lipman et al, "Rapid and Sensitive Protein Similarity Searches", Science, vol. 227, pp. 1435–1441, Mar. 22, 1985.
Altschul et al, "Basic Local Alignment Search Tool", J. Mol. Biol. (1990) 215, 403–410.
Baldi et al, "Hidden Markov Models of Biological Primary Sequence Information", Proc. Natl. Acad. Sci. US. vol. 91, pp. 1059–1063, Feb. 1994.
Obata N et al: "A Method for Information Analysis of Sequences by Two–Dimensional Pattern Formation with Coloration" Proceedings of The First International Conference. Quantum Information, Proceedings of First International Conference on Quantum Information, Nagoya, Japan, Nov. 4–8, 1997, pp. 27–58, XP000961400 1999, Singapore, World Scientific, Singapore ISBN: 981–02–3934–3 *p. 31, Paragraph 2.1–p. 33, Paragraph 2.2*.
Maizel J V et al: "Enhanced Graphic Matrix Analysis of Nucleic Acid and Protein Sequences" Proceedings of The National Academy of Sciences of the USA, US, New York, NY, vol. 78, No. 12, Dec. 1, 1981, pp. 7665–7669, XP002036657 *p. 7666, Right–Hand Column, Line 57–62**p. 7666, Right–Hand Column, Line 19–21*.
X. Guan et al.: "A Fast Look–Up Algorithm for Detecting Repetitive DNA Sequences" Jan. 6, 1996, World Scientific, San Francisco, USA XP000953382 *The Whole Document*.
Hiromitsu Yokoo et al, ICARUS, 38, 148–153 (1979), "Is Bacteriophage ΦX174 DNA a Message from an Extraterrestrial Intelligence?"
Thompson et al., Nucleic Acids Reseach, vol. 22, No. 22, pp. 4673–4680, 1994.*

\* cited by examiner

*Primary Examiner*—Ardin H. Marschel
(74) *Attorney, Agent, or Firm*—Oblon, Spivak, McClelland, Maier & Neustadt, P.C.

(57) ABSTRACT

A method for expressing at least one characteristic existing in a symbolic sequence that begins with a known single symbolic sequence that is broken down into smaller non-overlapping portions and then placed in parallel to reveal previously unrecognized characteristics in the entire symbolic sequence.

31 Claims, 18 Drawing Sheets

(11 of 18 Drawing Sheet(s) Filed in Color)

| k=2 | | k=3 | | | k=4 | | | | k=20 | | | | | | |
|---|---|---|---|---|---|---|---|---|---|---|---|---|---|---|---|
| 1 | | 1 | 2 | | 1 | 2 | 3 | | 1 | 2 | 3 | 4 | | 1 | 2 | 3 | · | · | · 20 |

(Table representation is approximate; see figure.)

| k=2 | k=3 | k=4 | k=20 |
|---|---|---|---|
| 1 | 1 2 | 1 2 3 | 1 2 3 · · · 20 |
| 2 | 3 4 | 4 5 6 | 21 · · · · · |
| 3 | 5 6 | 7 8 9 | · · · · · · |
| 4 | 7 8 | 10 11 12 | · · · · · · |
| 5 | 9 10 | 13 14 15 | · · · · · 100 |
| 6 | 11 12 | 16 17 18 | |
| 7 | 13 14 | 19 20 · | |
| 8 | 15 16 | · · · | |
| 9 | 17 18 | · · · | |
| 10 | 19 20 | · · · | |
| 11 | · | | |
| 12 | · | | |
| 13 | · | | |
| 14 | | | |
| 15 | | | |
| 16 | | | |
| 17 | | | |
| 18 | | | |
| 19 | | | |
| 20 | | | |
| · | | | |
| · | | | |
| · | | | | k=4 column: 1 2 3 4 / 5 6 7 8 / 9 10 11 12 / 13 14 15 16 / 17 18 19 20

| 1 | 5 10 |
| 2 | 15 20 |
| 3 | 25 30 |
| 4 | 35 40 |
| 5 | 45 50 |
| 6 | 55 60 |
| 7 | 65 70 |
| 8 | 75 80 |
| 9 | 85 90 |
| 10 | 95 | k=3

| | k=2 | k=3 | k=4 | k=20 |
|---|---|---|---|---|
| 1 | 1  2 | 1  2  3 | 1  2  3  4 | 1  2  3  .  .  . 20 |
| 2 | 4  3 | 6  5  4 | 8  7  6  5 | .  .  . 22 21 |
| 3 | 5  6 | 7  8  9 | 9 10 11 12 | |
| 4 | 8  7 | 12 11 10 | 16 15 14 13 | |
| 5 | 9 10 | 13 14 15 | 17 18 19 20 | |
| 6 | 12 11 | 18 17 16 | . . . . | . . . . . 100 |
| 7 | 13 14 | 19 20  . | . . . . | |
| 8 | 16 15 | . . . | . . . . | |
| 9 | 17 18 | . . . | . . . . | |
| 10 | 20 19 | . . . | | |
| 11 | . | | | |
| 12 | . | | | |
| 13 | . | | | |
| 14 | | | | |
| 15 | | | | |
| 16 | | | | |
| 17 | | | | |
| 18 | | | | |
| 19 | | | | |
| 20 | | | | |

*FIG. 16*

METHOD AND APPARATUS FOR REVEALING LATENT CHARACTERISTICS EXISTING IN SYMBOLIC SEQUENCES

BACKGROUND OF THE INVENTION

1. Field of the Invention

The present invention relates to a method and apparatus for manifesting a characteristic or regularity which is latent and can not be recognized, although such characteristic or regularity actually exists in a complicated symbolic sequence, for example, a nucleotide sequence of DNA, an amino acid sequence of protein, or a digital sequence of decimal expansion of an irrational number and the like. In these sequences, regularity can not be recognized at a glance even when the regularity is included. The present invention enables recognition of characteristic a or regularity included in the symbolic sequence but not yet unrecognized.

2. Description of the Related Art

Some complicated symbolic sequences contain characteristic which has not been recognized by human beings, although the characteristic actually exists. For example, genetic information is specified by a symbolic sequence of long string. The symbols consist of four symbols each indicating one of four kinds of nucleotides. A large number of symbols are one-dimensionally aligned. In the study of genetic information, it is extremely important to recognize a certain regularity hidden in the symbolic sequence indicating genetic information. Besides, if a certain regularity is found in an irrational number, the number $\pi$, and the base of natural logarithm (e), the study of random numbers is intensified and various developments are expected in mathematics.

For such a purpose, various trials have been made for analyzing a symbolic sequence based on a variety of mathematical methods such as the Fourier analysis. However, these trials have not necessarily accomplished successful results. One problem with the conventional analysis methods is that even if a certain regularity is included in a part of a very long symbolic sequence, the latent regularity is buried within the whole sequence and can not be recognized when the whole symbolic sequence is analyzed. Since there is no effective technology to determine in advance in which part of the sequence the regularity exists, there are many characteristics or regularity which can not be recognized by the conventional analysis methods.

SUMMARY OF THE INVENTION

An object of the present invention is to provide a method and apparatus which manifests a characteristic or regularity even if such characteristic or regularity exists only in a part of the whole symbolic sequence, and thereby enables recognition of a characteristic or regularity which has not been recognized until now.

Another object of the present invention is to manifest a characteristic or regularity existing throughout the entire sequence.

In one embodiment of the present invention, when a symbolic sequence $I_j$ (j=1~m) is given, there is an effected conversion to a parallel sequence A(k) of partial symbolic sequences in which the suffix j is aligned in the following positional relation:

j=1, 2, . . . k−1, k
j=k+1, k+2, . . . k+k−1, k+k
:
:
:
j=(n−1)k+1, (n−1)k+2, . . . (n−1)k+k−1, (n−1)k+k
j=nk+1, nk+2, . . . nk+k−1, nk+k.

In the alternative, the positional relation may be the following:

j=1, 2, . . . k−1, k
j=k+k, k+k−1, . . . k+2, k+1
:
:
:
j=(n−1)k+k, (n−1)k+k−1, . . . (n−1)k+2, (n−1)k+1
j=nk+1, nk+2, . . . nk+k−1, nk+k.

Herein, k represents an integer of 2 or more, n represents an integer such that nk<m≦nk+k, and when the suffix j is m+1 or more, the processing is ignored.

Then, the converted parallel sequence A(k) is output using one or more expression means selected from hue, lightness and saturation of color and from interval, tone and volume of sound.

Equidistant Letter Sequences in the Book of Genesis (Doron Witztum, Eliyahu Rips and Yoav Rosenberg, Statistical Science 1994, Vol. 9, No. 3, page 429–438) introduces a technology in which a code hidden in a one-dimensional letter sequence is decoded by converting the one-dimensional letter sequence to a parallel sequence A(k) of partial symbolic sequences. In this technology, there is required an operation to extract letters having senses from the parallel sequence A(k) of partial symbolic sequences, and it can not be used for other sequences than the letter sequence. Further, when a certain regularity is to be recognized in a symbolic sequence which is irregular at a glance and which is often found in a natural field, inconsistency, namely, regularity can not be recognized unless the regularity to be recognized has been recognized in advance, can not be solved.

In the present invention described above, since a parallel sequence A(k) of partial symbolic sequences is output using one or more expression means selected from hue, lightness and saturation of color and from interval, tone and volume of sound, even if regularity is not known in advance, that regularity is manifested by a pattern of hue, lightness and saturation of color and interval, tone and volume of sound and can be easily recognized.

In another embodiment of the present invention, when a one-dimensional symbolic sequence $I_j$ (j=1~m) is given, there is an effected conversion to a parallel sequence A(k) of partial symbolic sequences in which the suffix j is aligned in the following positional relation:

j=1, 2, . . . k−1, k
j=k+1, k+2, . . . k+k−1, k+k
:
:
:
j=(n−1)k+1, (n−1)k+2, . . . (n−1)k+k−1, (n−1)k+k
j=nk+1, nk+2, . . . nk+k−1, nk+k.

In the alternative, the positional relation may be the following:

j=1, 2, . . . k−1, k
j=k+k, k+k−1, . . . k+2, k+1
:
:
:
j=(n−1)k+k, (n−1)k+k−1, . . . (n−1)k+2, (n−1)k+1
j=nk+1, nk+2, . . . nk+k−1, nk+k.

Further, when p represents a natural number from 2 to less than m, r represents any natural number, the above-described conversion is repeated with changing k to p, p+r, p+2r, p+3r, . . . to obtain parallel sequences of partial symbolic sequences: A(p), A(p+r), A(p+2r), A(p+3r) . . . . Then, the resulted parallel sequences: A(p), A(p+r), A(p+2r), A(p+3r) . . . are further parallel-positioned to make a whole parallel sequences ΣA(k). Then, the obtained whole parallel sequences ΣA(k) is output. Here, n represents an integer such that nk<m≦nk+k, and when the suffix j is m+1 or more, the processing is ignored.

In this case, a parallel sequence made by parallel-positioning of p partial symbolic sequences, a parallel sequence made by parallel-positioning of p+r partial symbolic sequences, and parallel sequences made by parallel-positioning of likewise increased number of partial symbolic sequences, are all parallel-positioned. In this processing, if regularity of period length α is hidden in the symbolic sequence, such regularity is remarkably manifested in a parallel sequence A(α) made by parallel-positioning of partial symbolic sequences of a number of α.

If α is included in between p, p+r, p+2r, p+3r, . . . rows, regularity of period length α a is manifested in a parallel sequence of partial symbolic sequences of an analogous number to α. Therefore, increment r regarding the number of the partial symbolic sequences is not necessarily required to be one, and it may advantageously be any natural number. In this case, when the increment r is smaller, the characteristic is more easily manifested.

In this embodiment, regularity of an unknown period length is manifested in a parallel sequence of partial symbolic sequences of some number, and recognition of the characteristic becomes easy.

In the above-described method, it is preferable that each symbol is expressed by a combination of hue, lightness and saturation of color. By this embodiment, as a result of the manifestation of the characteristic hidden in the symbolic sequence through visual means, a more complete understanding regarding the characteristic hidden in the symbolic sequence is possible, and various applications and developments utilizing the characteristic are made possible. Further, the resulting visual pattern is a pattern including mixed regularity and irregularity mixed which has not previously existed, and a visual pattern of which design itself has utility application can be designed.

Each symbol may be expressed by a combination of interval, tone and volume of sound. By expressing the parallel sequence by a combination of interval, tone and volume of sound, a unique audio pattern is created and the characteristic of the symbolic sequence can be recognized through auditory means.

When one symbol is taken out from an original symbolic sequence at an interval of k−1 (namely, at every k) to make a symbolic sequence and the method is applied to this extracted symbolic sequence, if regularity of period length k is hidden in the original symbolic sequence, the regularity is manifested and appears remarkably.

When one symbol is taken out from an original symbolic sequence at an interval of kq−1 (namely, at every kq) to make a symbolic sequence and the method is applied to this extracted symbolic sequence, if regularity of period length kq is hidden in the original symbolic sequence, the regularity is manifested and appears remarkably.

Further, when any of the above-described methods are conducted with changing k to p, p+r, p+2r . . . , there is formed a whole parallel sequences ΣA(k) of a parallel sequence A(p) made by parallel-positioning of p partial symbolic sequences, a parallel sequence A(p+r) made by parallel-positioning of p+r partial symbolic sequences, and parallel sequences made by parallel-positioning of likewise increased number of partial symbolic sequences, and regularity of period length α appears remarkably in a parallel sequence A(α) formed by parallel-positioning of k (=α) partial symbolic sequences. Therefore, characteristic or regularity of unknown period length is manifested, and recognition of characteristic or regularity becomes easy.

According to this method, even if the period length α of regularity or characteristic is included between p, p+r, p+2r, . . . rows, characteristic or regularity is manifested in a parallel sequence formed by parallel-positioning partial sequences of a number approximated to α, and increment r is not necessarily required to be one. It becomes possible to manifest the characteristic using a small amount of data processing, by selecting increment r which has been adjusted to the situation.

Further, by outputting analyzed results by color and/or sound, expressions suitable to situation and observer become possible, and the characteristic is more easily recognizable. The resulting color and/or sound pattern will be an interesting pattern in which regularity and irregularity are mixed, and the method can be utilized also as a designing method.

Especially when an initiation position of regularity is situated at an analysis initiation position, the pattern of having a parabolic shape clearly appears, and regularity of a long period length is manifested clearly, in the whole parallel sequences ΣA(k).

The present invention will be recognized more successfully by reading the descriptions of the following examples with the referring drawings.

BRIEF EXPLANATION OF THE DRAWINGS

The file of this patent contains at least one drawing executed in color. Copies of this patent with color drawing(s) will be provided by the Patent and Trademark Office upon request and payment of the necessary fee.

FIG. 10 represents placing positions in converting 100 symbolic sequence into the whole parallel sequences ΣA(k).

FIG. 12 represents another example of placing positions in converting a symbolic sequence into the whole parallel sequences ΣA(k).

FIG. 16 represents another positioning (reciprocal) pattern for obtaining a parallel sequence A(k).

DETAILED DESCRIPTION OF THE PREFERRED EMBODIMENTS

Experimental examples embodying the present invention will be introduced below.

First Experimental Example

Figure 1:
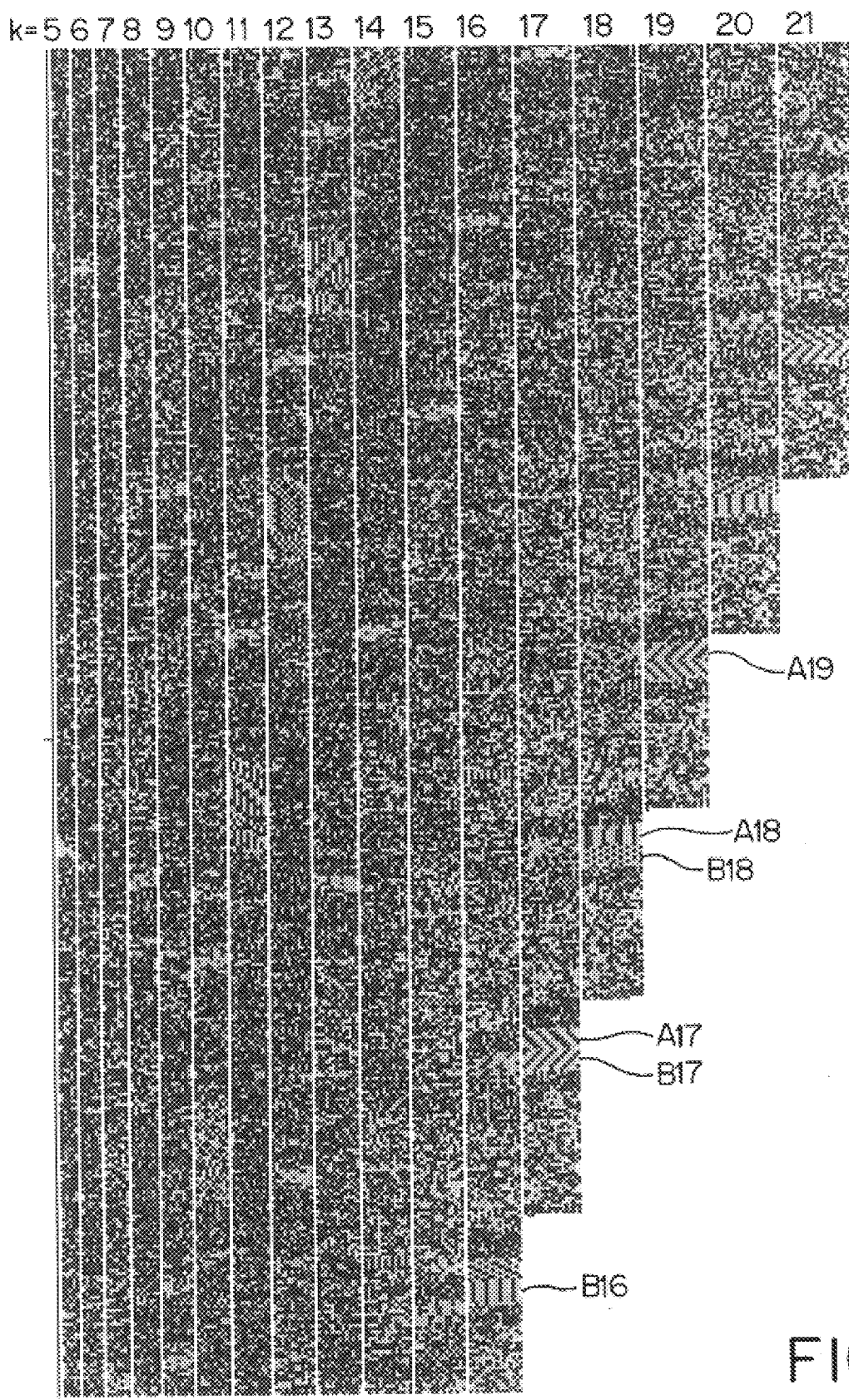
FIG. 1 represents the whole parallel sequences ΣA(k) formed from a nucleotide sequence of human genomic DNA.

FIG. 1 represents an experimental example for processing a symbolic sequence $I_j$ showing a nucleotide sequence of human genomic DNA. A symbolic sequence $I_j$ indicating nucleotide sequence of human genomic DNA is formed by one-dimensional sequence of an enormous number of symbols, each symbol indicating one of four kinds of nucleotides ATGC, and a certain regularity hidden therein is recognized as useful information. Therefore, it is an important aspect of genetic study to find regularity, or to specify a part of the sequence including the regularity.

FIG. 1 represents a processed result output using color, and the four kinds of symbols ATGC are, respectively, expressed by four colors red, blue, green and yellow. The original image of FIG. 1 is expressed in four colors. FIG. 1 represents a result when the present invention is conducted with p=5 and r=1.

Figure 2:
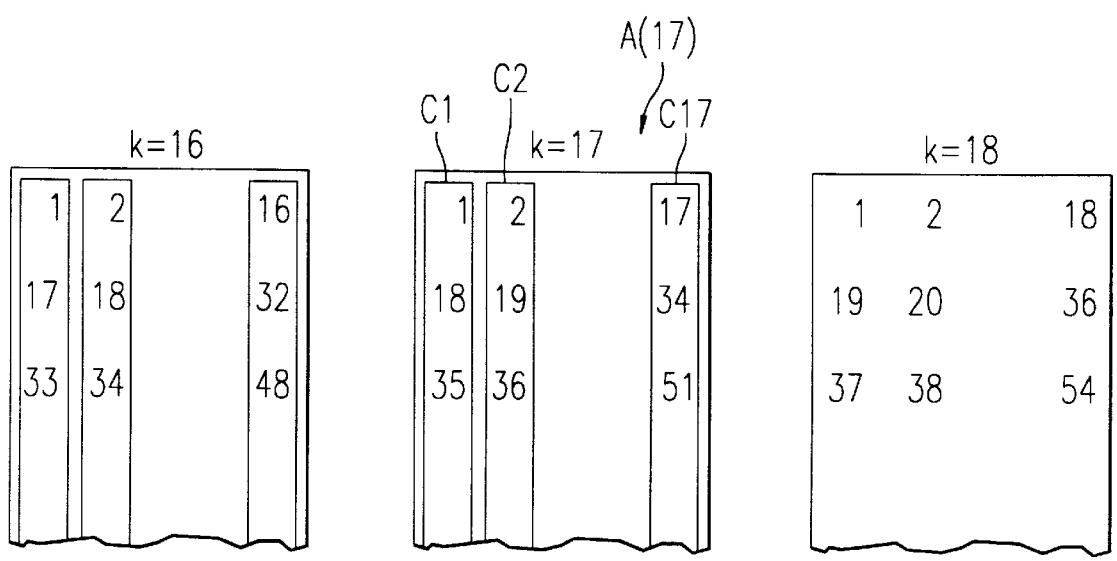
FIG. 2 represents positional relation of suffix j in FIG. 1.

Referring to an example of a parallel sequence A(17) in which k=17, as shown in FIG. 2, longitudinal partial symbolic sequences C1, C2, C3 . . . C17 which are extracted from a symbolic sequence $I_j$ at every k and aligned longitudinally, are laterally aligned to form a parallel sequence A(17). In columns C1, C2, C3 . . . the values of symbol suffixes j to be extracted are shifted by one. This rule is common to all k values and to all partial symbolic sequences C.

In this example, a symbol group extracted at every k is placed longitudinally (i.e., in columns) to form a longitudinal partial symbolic sequence, and the longitudinal partial symbolic sequences are laterally placed. However, longitudinal to lateral relations may be reversed, and a symbol group extracted at every k may be placed laterally to form a lateral partial symbolic sequence, and the lateral partial symbolic sequences may be longitudinally placed.

In FIG. 1, B16 remarkably shows that a repeating pattern of period length 16 exists in a part of the nucleotide sequence. From the pattern B16, it is possible to learn that there is a possibility that useful information is included in this part, and this part is an area that is valuable to be analyzed in detail. B17 and B18 represent the same regularity. The regularity of period length 16 appears as the vertical stripes in B16, and appears as the inclined stripes in B17. The inclined stripes in B17 have a pattern in which the left side is lowered. B18 also represents the same regularity, and the inclination of the stripes in B18 is closer to horizontal than in B17. The same regularity is also shown in a parallel sequence A(19) in which k=19, however, in this case, the inclination is almost horizontal, and extraction of characteristic becomes increasingly difficult.

Regularity of period length α appears vertically and is expressed most remarkably in A(α) in which k (=α) partial symbolic sequences are parallel-positioned. However, the regularity also appears in a parallel sequence of partial symbolic sequences in which k=α+1 and k=α+2. Therefore, it is confirmed that the increment r is not necessarily required to be 1.

A18 shows regularity of period length 18, and the same regularity is shown as pattern A17 in which the right side is lowered in the parallel sequence A(17) in which k=17, and shown as pattern A19 in which the left side is lowered in the parallel sequence A(19) in which k=19.

In addition, many remarkable patterns appear in FIG. 1, and characteristics hidden in a nucleotide sequence of human genomic DNA can be recognized from these patterns.

Initial number p in the whole parallel sequences of partial symbolic sequences may be any natural number, and in FIG. 1, p=5. The increment r is not limited to 1, and it may be 2 or more. When r is smaller, characteristics always can be found, and when r is larger, the amount of data processing is smaller. The increment r is not required to be constant, and it is preferable to select the increment r according to situation.

Figure 18:
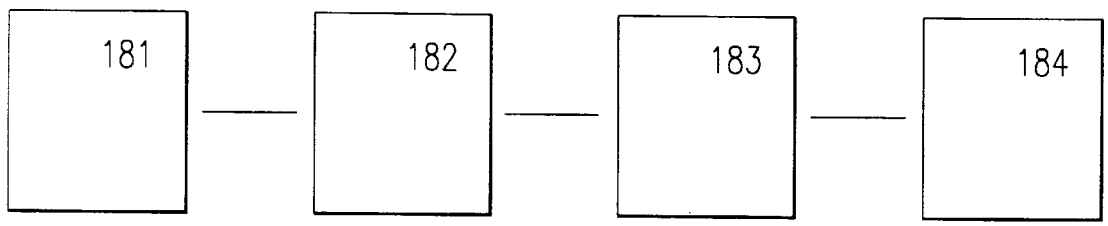
FIG. 18 represents constitution of an apparatus for effecting the method of the present invention.

FIG. 18 represents an apparatus for effecting the above-described processing method, and in this apparatus, a symbolic sequence $I_j$ to be analyzed is stored in a memory apparatus 181, and an apparatus 182 converts the symbolic sequence Ij into a parallel sequence A(k), and apparatus 183 forms the whole parallel sequences ΣA(k) in which a plurality of parallel sequences A(k) obtained by changing the value of k are parallel-positioned, and an apparatus 184 outputs the whole parallel sequences ΣA(k). The apparatus 182 and the apparatus 183 may be a computer and the apparatus 184 may be a color printer. When the whole parallel sequences ΣA(k) is output using sound, a sound synthesizer may be used as the apparatus 184.

It is preferable that FIG. 1 is expressed with a time lapse according to speed for processing the symbolic sequence. For example in FIG. 1, color corresponding to I1 is first expressed on the left upper summits of A(5) to A(21), and further expressions of I2, I3, I4 . . . are effected in succession. By using this change in time, characteristics are more easily recognized, and also in the case of output by sound, output with time lapse is effective, and when output with time lapse is conducted, characteristics are recognized through changes in sound.

Figure 3:
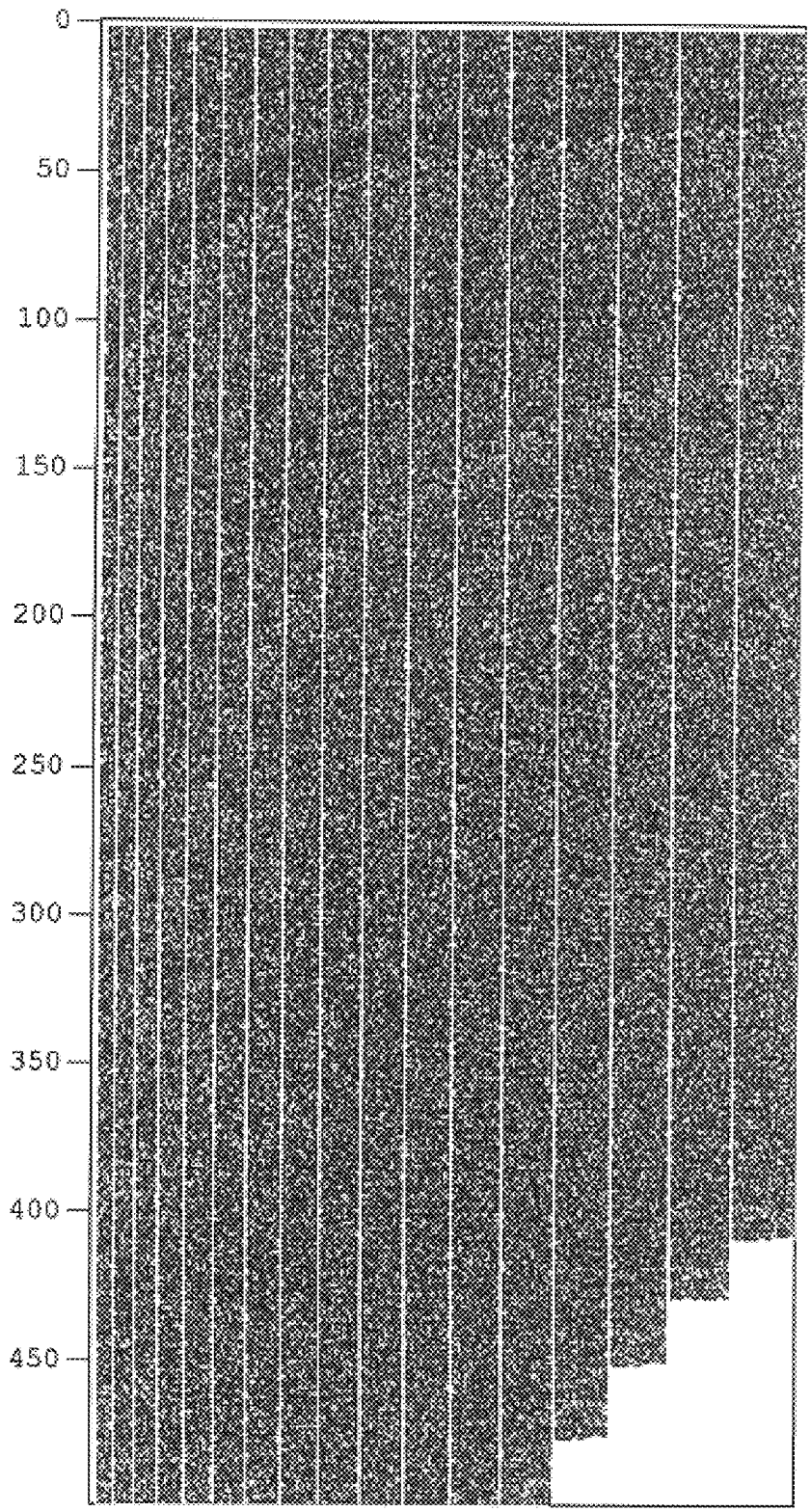
FIG. 3 represents the whole parallel sequences ΣA(k) formed from a numerical sequence showing π.

FIG. 3 exemplifies a result obtained by processing π as a symbolic sequence (numerical sequence), and the 10 kinds of symbols (numbers) 0 to 9 are expressed using 10 equally divided colors of the spectrum from a violet to red. It was found from the expression result of FIG. 3 that specific symbols (numbers) tend to appear frequently in a specific range.

When noise input is processed as a row of a symbolic sequence and this symbolic sequence is processed to obtain a similar pattern as in FIG. 3, it becomes possible to extract a characteristic existing in the noise and to extract only meaningful sound included in the noise. Further, it is known that the pattern shown in FIG. 3 can be used, for example, as a ground pattern for securities, and this complicated ground pattern can be specified by a one-dimensional symbolic sequence.

Figure 4:
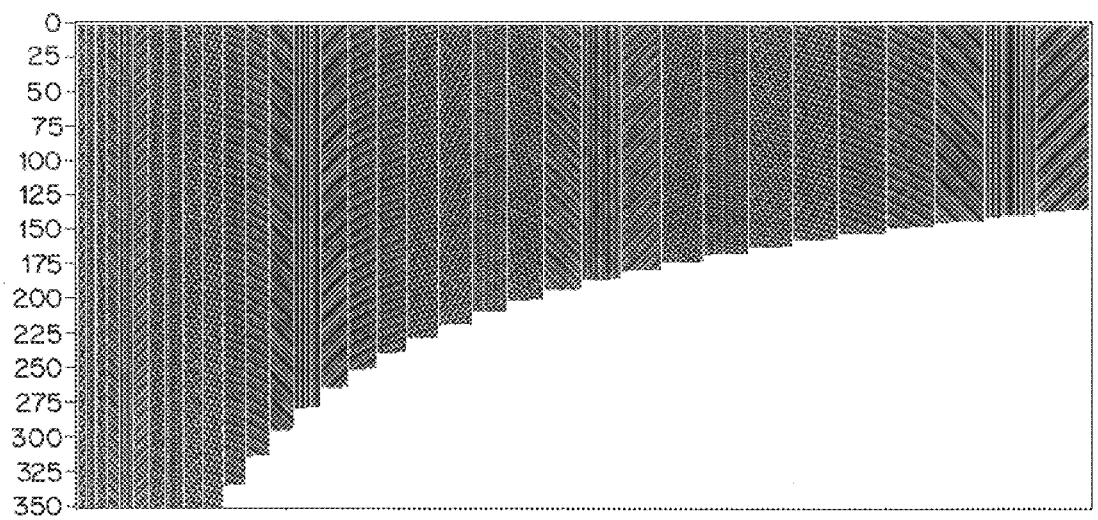
FIG. 4 represents the whole parallel sequences ΣA(k) formed from a circulating numerical sequence of period length 18 (symbolic sequence).
Figure 5:
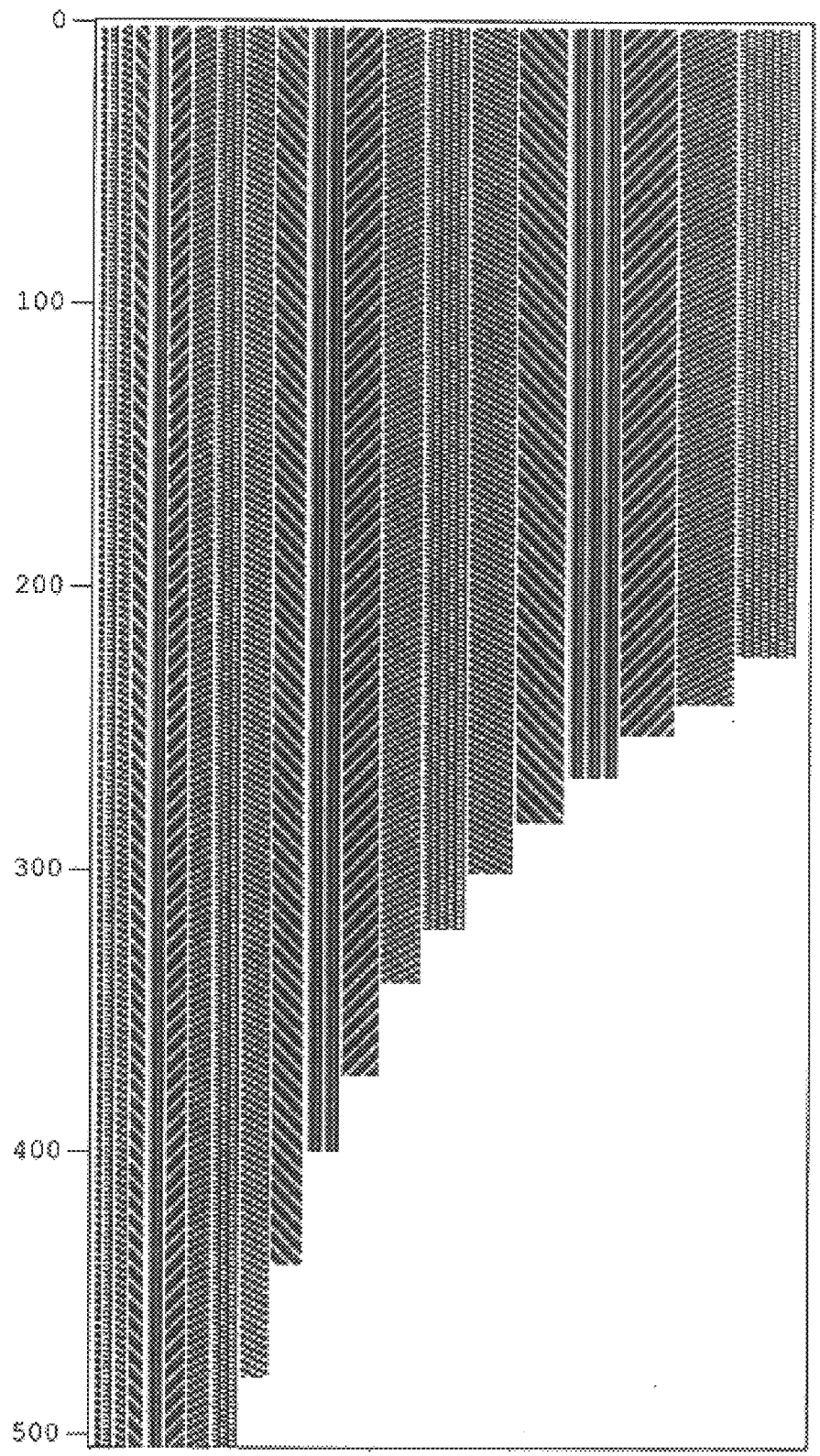
FIG. 5 represents the whole parallel sequences ΣA(k) formed from a circulating numerical sequence of period length 12 (symbolic sequence).

FIG. 4 represents a result obtained by processing a circulating numerical sequence of period length 18, and various patterns can be drawn according to the number k of a partial symbolic sequences to be fractionated. Various textile patterns can be designed by this pattern creating technology. FIG. 5 represents a processed result of a circulating numerical sequence of period length 12, and it is confirmed that different patterns from those of FIG. 4 can be made. According to this method, the complicated pattern shown in FIG. 3 and the regular patterns shown in FIGS. 4 and 5 can be designed by the same method. Further, various patterns having utterly different impressions can be produced by changing corresponding relations of a symbol to a color.

Figure 6:
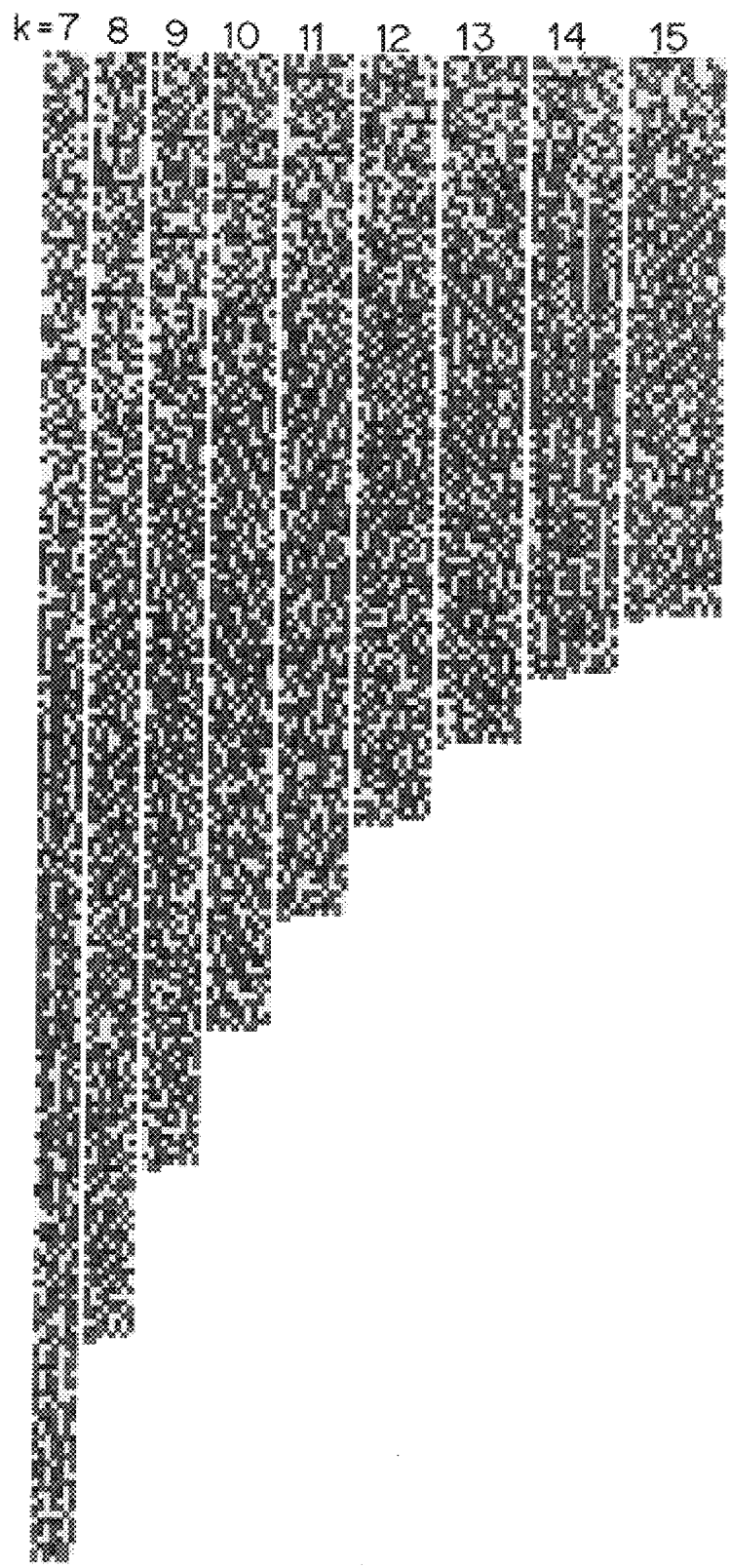
FIG. 6 represents a part of the whole parallel sequences ΣA(k) formed from an amino acid sequence of muscle protein myosin.
Figure 7:
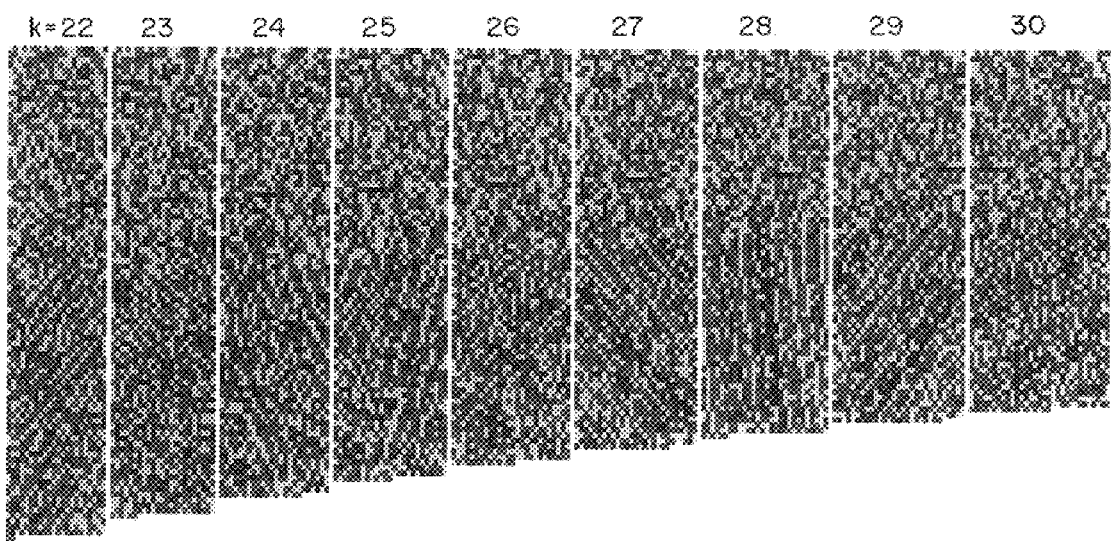
FIG. 7 represents another part of the whole parallel sequences ΣA(k) formed from the amino acid sequence of muscle protein myosin.
Figure 8:
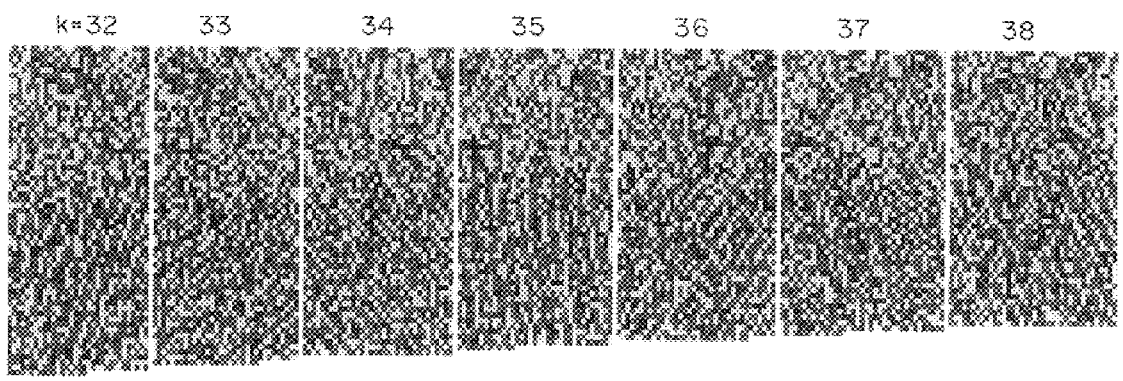
FIG. 8 represents still another part of the whole parallel sequences ΣA(k) formed from the amino acid sequence of muscle protein myosin.

FIGS. 6 through 8 represent a result obtained by processing a symbolic sequence which shows an amino acid sequence of a protein myosin of an adductor muscle of a scallop. In FIGS. 6 to 8, basic residues are shown in blue, polar residues are shown in green, acidic residues are shown in red, and hydrophobic residues are shown in yellow. In FIG. 6, a remarkable yellow longitudinal stripe appears in a parallel sequence in which k=7, and the existence of regularity of a period length 7 is found. This regularity of a hydrophobic residue of period length 7 corresponds an α-helix, and by this method, the existence of an α-helix can be recognized and the existing position thereof can be specified. This α-helix is manifested as yellow longitudinal stripes in parallel sequences in which k=7, 14, 28 and 35, and manifested as yellow diagonal lines in parallel sequences in which, for example, k=22, 27 and 29.

Figure 9:
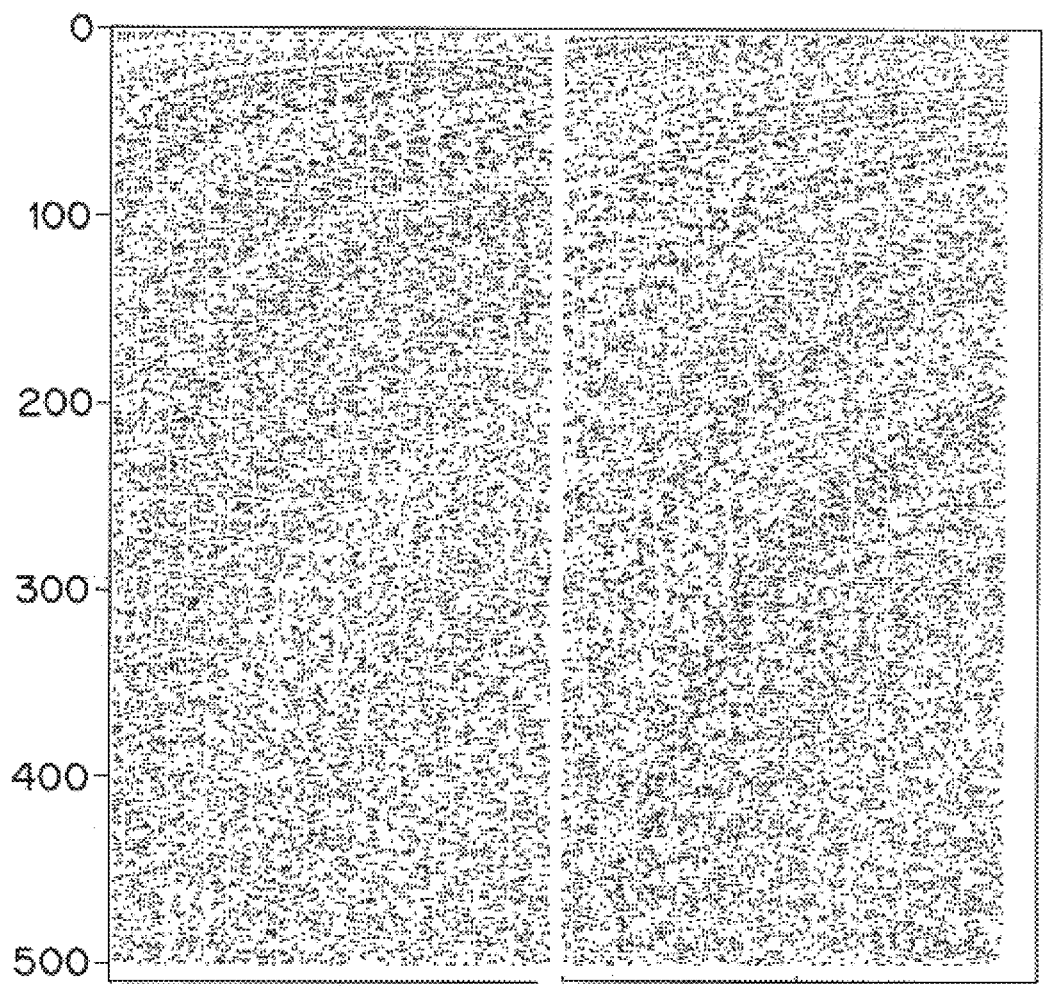
FIG. 9 represents existing positions of vowel 'O' appearing in 'Genji Monogatari'.

FIG. 9 represents an example expressing dots in positions where the vowel 'O' appears, prepared by applying the present invention to a symbolic sequence showing a row of vowels in Genji Monogatari. The left side represents an analysis result of the Kiritsubo chapter, and the right side represents an analysis result of the Hahakigi chapter. There is manifested characteristic that appear with frequency in vowel 'O' as high in the specific range of the document, and as low in other specific ranges. By this method, extraction of characteristic in alphabet information becomes easy.

FIG. 10 schematically represents processing contents for a symbolic sequence $I_j$ (j=1 to 100) to be processed.

When, the period length of regularity to be extracted is known in advance, it will be easily recognized whether the regularity of the known period length k really exists, and in the case of existence, where it exists, by forming a parallel sequence A(k) in which partial symbolic sequences obtained by division into k fractions are parallel-positioned.

Even when the period length is not known, regularity of the unknown period length is manifested at some location in the whole parallel sequences.

Figure 11:
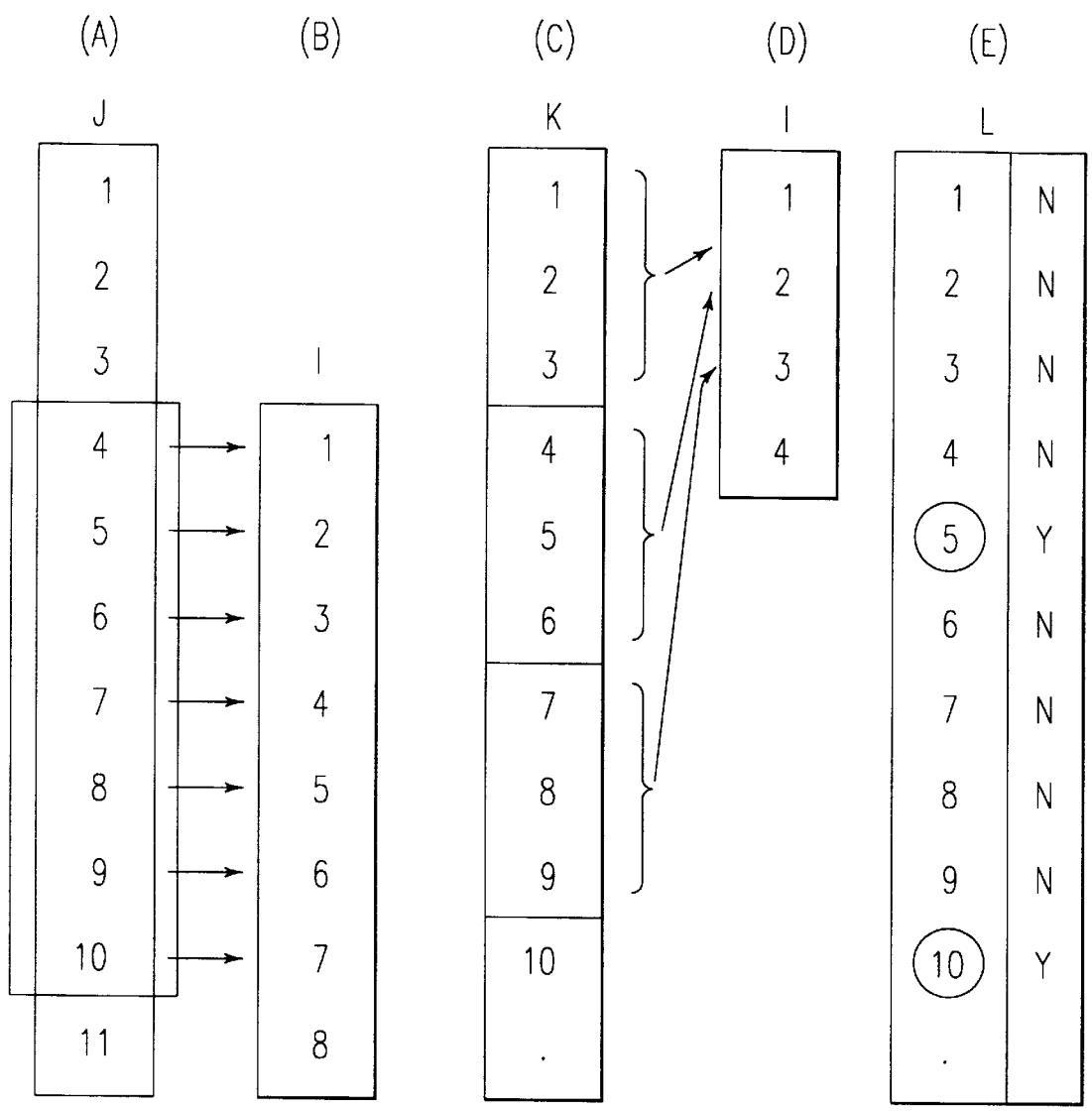
FIG. 11 explains pre-treatments for symbolic sequences.

FIG. 11 represents an example of pre-processing for a symbolic sequence to be processed, and when part of a symbolic sequence J shown in (A) is processed, the part to be processed as shown in (B) will be the whole symbolic sequence I of the present invention. Further, when one symbol is specified by a combination of a plurality of symbols, this method is applied for the symbolic sequence specified by a combination of a plurality of symbols, for example, as shown in (C). Alternatively, it may also be permissible that one symbol is obtained from symbols of order 123 in a symbolic sequence K, then, one symbol is obtained from symbols of order 234 in a symbolic sequence K, this procedure is repeated to effect conversion into one symbolic sequence I, and this converted symbol I is processed by the method, as in the case for calculating a moving average. Further, as shown in (E), for a symbolic sequence existing in a symbolic sequence at specific period, it may also be permissible that a symbolic sequence of this period is first extracted, and the present invention is applied to the extracted symbolic sequence.

Instead of this method, processing as exemplified in FIG. 12 may be effected. In this method, one symbol is extracted at every kq, for a partial symbolic sequence of longitudinal direction. In the case shown in this drawing, the result is obtained by effecting the method with changing k to 2, 3, 4 . . . and q is fixed at 5. The result corresponds to the result when a symbol of an order of 5·10·15 . . . is first extracted, and then the extracted sequence is separated into k partial symbolic sequences, and the resulting partial sequences are parallel-positioned to obtain a parallel sequence. By this method, it is possible to manifest regularity further hidden in a symbolic sequence hidden in a symbolic sequence L (shown in (E) of FIG. 11).

When a parallel sequence of partial symbolic sequences are obtained as described above, various method can be adopted for expressing the result, and a method in which a symbol is expressed by color, a method in which a symbol is expressed by variation in color density and a method in which a symbol is expressed by a character (two dimensional pattern) may be adopted, and further, the resulted line and row of symbols may also be expressed by sound. In this case, a chord is made by an arrangement of symbols in line direction, and an arrangement in a row direction is expressed by changing this chord by time. By this procedure, it becomes possible to recognize a characteristic existing in a symbolic sequence through sound.

The present invention is useful for analyzing various symbolic sequences, and useful in analyzing a nucleotide sequence of DNA, a nucleotide sequence of RNA, an amino acid sequence of protein, a numerical sequence, a letter sequence, a sound sequence and the like. By this analysis, it becomes possible to specify an existing position of useful information and to extract useful information. Further, when this method is applied to two symbolic sequences which can not be distinguished at a glance, characteristics are manifested, and the identity can be easily judged. In this sense, characteristics and regularity manifested in this method are not restricted to a repeating pattern having a certain period, and characteristics found in distribution of appearing sequence are also manifested. Further, the increment r in the number of partial symbolic sequences is not necessarily required to be 1, and further, it is not required to be a constant number. By effecting this method according to k1, k2, k3 . . . distributing irregularly, characteristics existing in two or more symbolic sequences are manifested, and the identity is easily judged.

Figure 13:
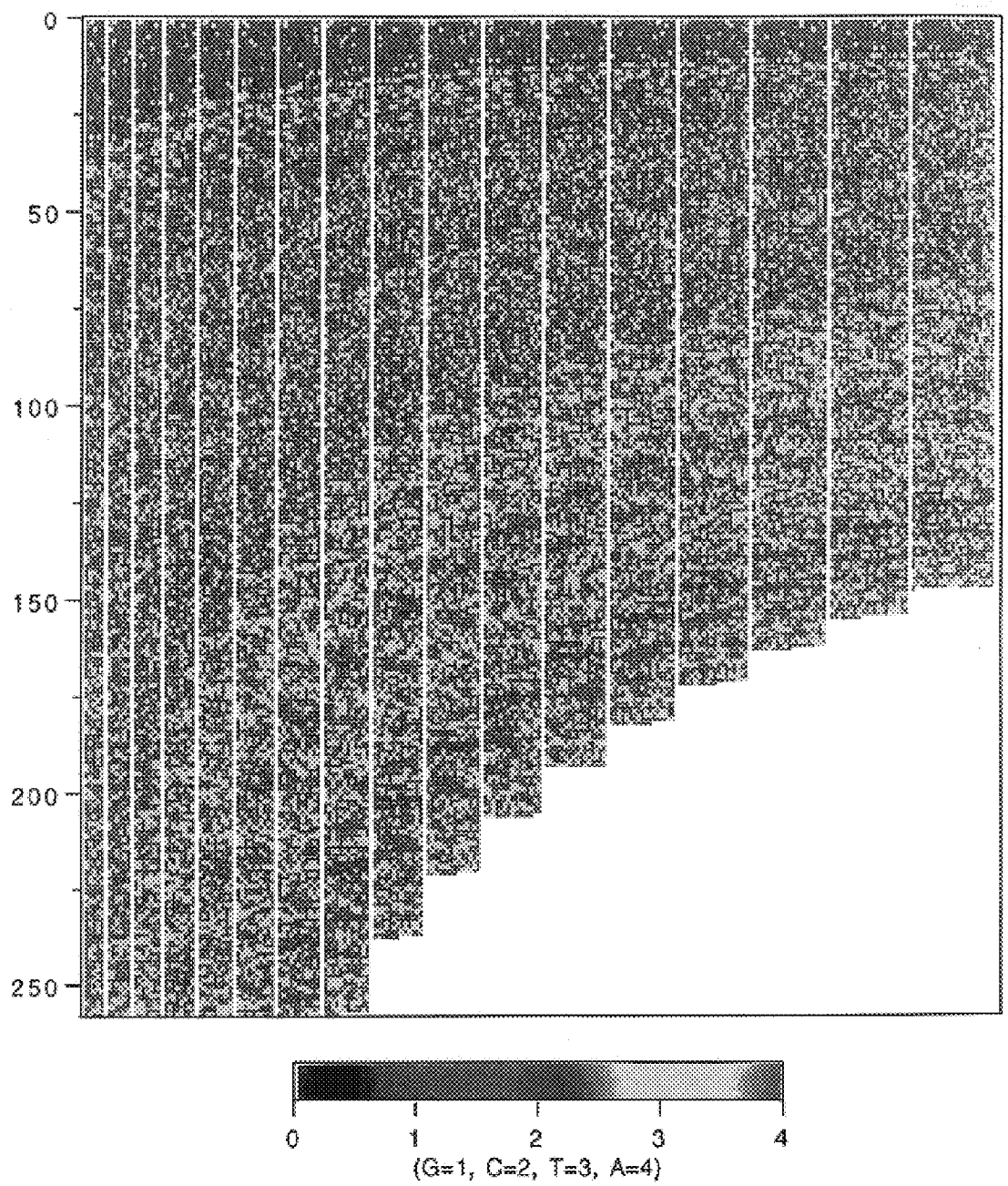
FIG. 13 represents the whole parallel sequences ΣA(k) formed from cDNA sequence of a G protein β subunit.

FIG. 13 represents the analysis result of a cDNA sequence of a G protein β subunit, and represents the result when the whole parallel sequences ΣA(k) is obtained when p is 5. In the original image of FIG. 13, GCTA are expressed by 4 colors and three apparent different color zones are recognized.

The boundary 101 of the color zones corresponds approximately to the position of j=281, and the boundary 102 of the color zones corresponds approximately to the position of j=1303. In this case, it is known that a coding range exists in the range from j=281 to j=1303, and it is recognized that the coding range is easily specified through visual sense in this method.

Figure 14:
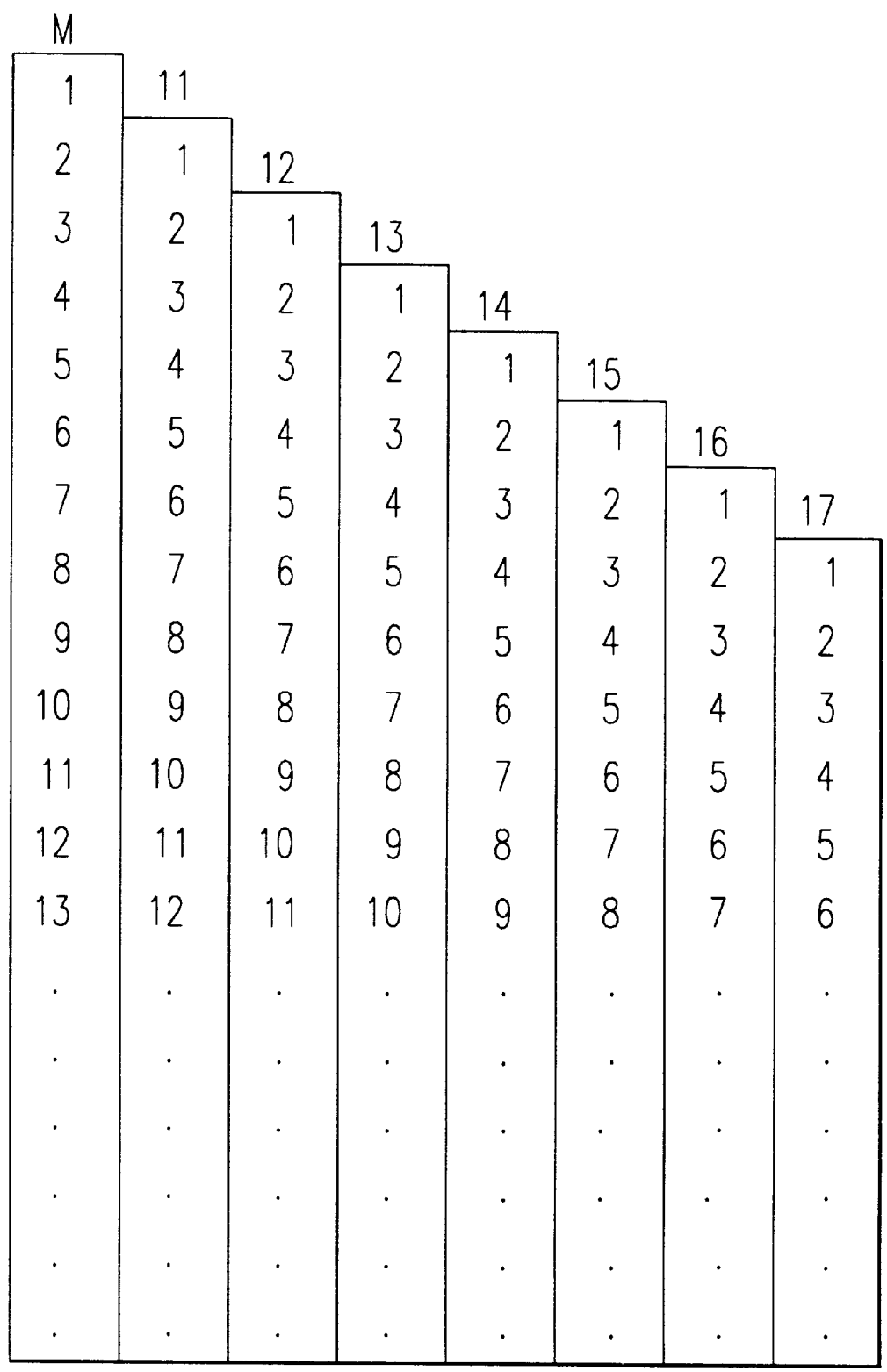
FIG. 14 represents extraction of symbolic sequence I to be processed with changing the initial point, from a symbolic sequence M.

FIG. 14 represents a procedure to obtain symbolic sequence I to be processed when changing the initial point, from a one-dimensional symbolic sequence M. For example, symbolic sequence I6 to be processed is a symbolic sequence obtained by extraction of M(6) and the following.

When the present invention is performed on symbolic sequences I1, I2, I3, I4 . . . thus extracted to obtain the whole parallel sequences ΣA(k), a clear pattern may be obtained in the whole parallel sequences ΣA(k) corresponding to a specific I.

Figure 15:
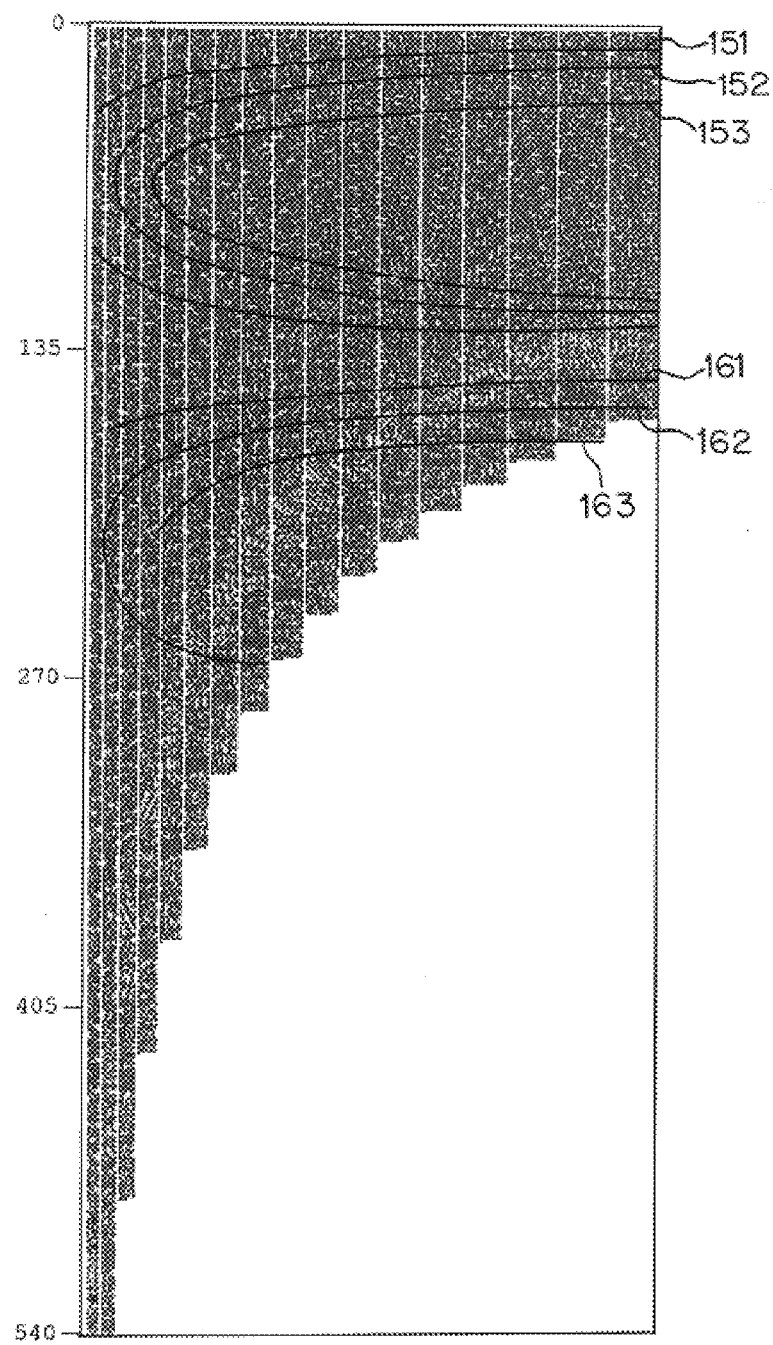
FIG. 15 represents an example in which parabolic pattern appears in the whole parallel sequences ΣA(k) formed from a genomic DNA sequence of baker's yeast.

FIG. 15 represents one example thereof, and in the original image which is expressed in multicolor, a plurality of parabolic lines 151, 152, 153 . . . appear.

As a result of intensive study of this phenomenon, it has been recognized that the above-described line group appears when the initiation point of regularity coincides with the initiation point of the symbolic sequence to be processed. By this, it has been known that the initiation point of regularity can be specified by utilizing appearance of a line group.

Further, it is also known that the appearance gap of a group of lines 151, 152, 153 . . . and other group of lines 161, 162, 163 . . . corresponds to regularity of an extremely long period, and it has also been recognized that the regularity of an extremely long period can be recognized by utilizing a line group.

Figure 17:
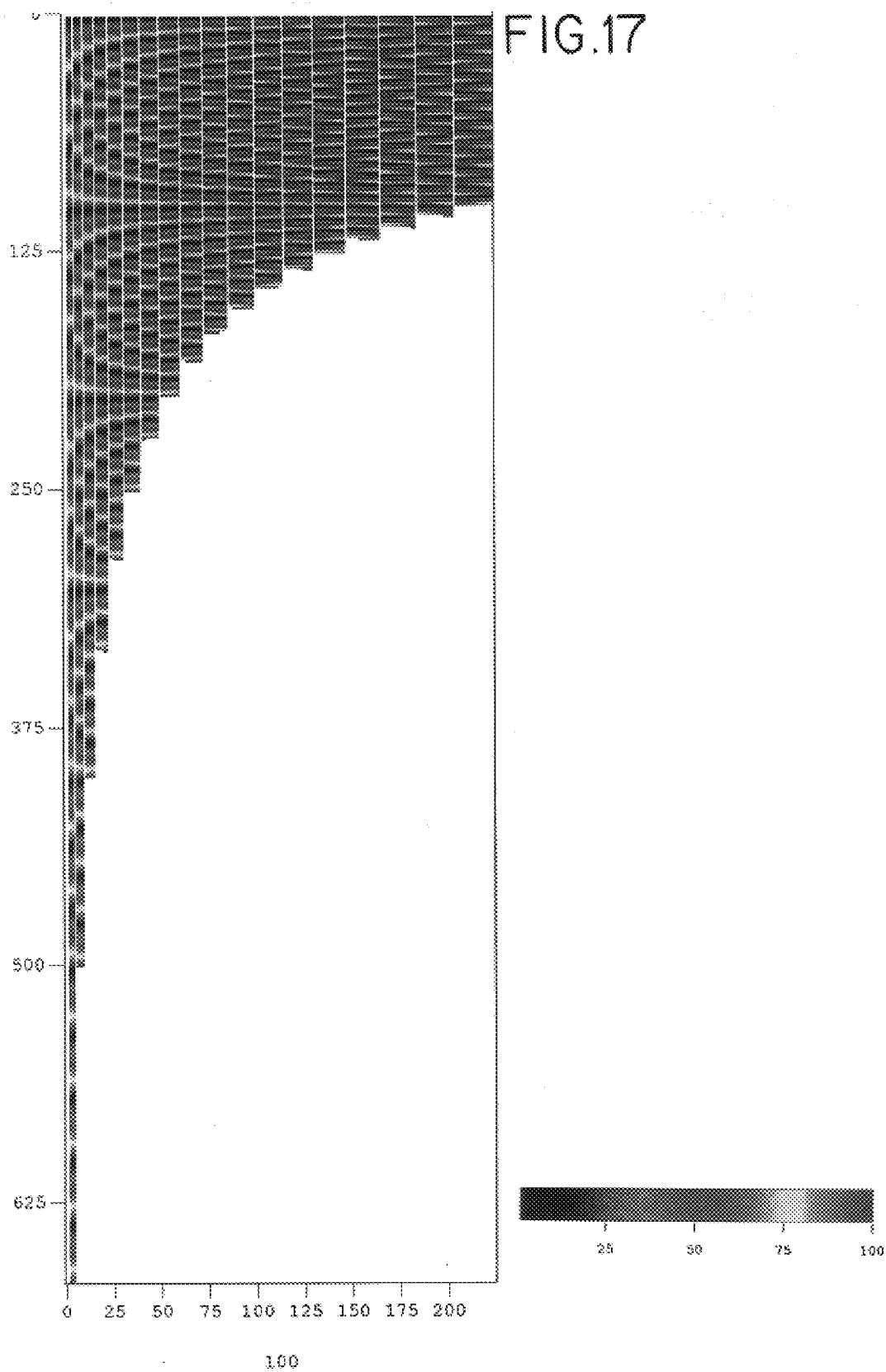
FIG. 17 represents the whole parallel sequences ΣA(k) formed from a circulating sequence of period length 100.

It has been recognized that the above-described pattern appears also by reversing alternately a sequential direction of partial symbolic sequences in a lateral direction (reciprocal positioning pattern). FIG. 16 represents a positional relation for obtaining a parallel sequence A(k) by reversing alternately a sequential direction of partial symbolic sequences in lateral direction. FIG. 17 represents an example in which a circulating sequence having a period of 100 is converted to the whole parallel sequences ΣA(k) having the positional relation as shown in FIG. 16, and it is recognized that a clear line group appears.

The above-described explanations are only some specific examples and the present invention can be used in various ways within the attached claims.

What is claimed is:

1. A method of expressing a characteristic in alphanumeric data comprising at least a first alphanumeric data representation and a second alphanumeric data representation, the method comprising:
   using a computer processor to:
   (i) convert a single linear sequence of the alphanumeric data into at least a first matrix of alphanumeric data, a second matrix of alphanumeric data and a third matrix of alphanumeric data, the first matrix having X columns, the second matrix having Y columns and the third matrix having Z columns, wherein X, Y, Z are integers that are equal or greater than 2 and X, Y and Z are each different integers,
   (ii) assign a first color to the first alphanumeric data representation and
   (iii) assign a second color to the second alphanumeric data representation,
      wherein the first color and the second color are different from each other, and visually displaying the first, second and third matrices of colors in a proximal relationship.

2. The method according to claim 1, wherein the alphanumeric data is nucleotide sequence data comprising at least 4 different alphanumeric nucleotide representations and at least 4 different colors are assigned to the at least 4 different alphanumeric nucleotide representations.

3. The method according to claim 1, wherein the at least first, second and third matrices are visually displayed side-by-side.

4. The method according to claim 1, wherein Y equals X+r and Z equals X+2r, wherein r is an integer.

5. The method according to claim 4, wherein the alphanumeric data is nucleotide sequence data comprising at least 4 different alphanumeric nucleotide representations and at least 4 different colors are assigned to the at least 4 different alphanumeric nucleotide representations.

6. The method according to claim 5, wherein the at least first, second and third matrices are visually displayed side-by-side.

7. The method according to claim 6, wherein the at least 4 different colors are different from a background color against which the at least 4 different colors are displayed.

8. The method according to claim 1, wherein the first and second colors are different from a background color against which the first color and the second color are displayed.

9. A method of identifying a repeating sub-sequence within a single linear sequence of alphanumeric data comprising at least a first alphanumeric data representation and a second alphanumeric data representation, the method comprising:
   converting the single linear sequence of the alphanumeric data into at least a first matrix of alphanumeric data, a second matrix of alphanumeric data and a third matrix of alphanumeric data, the first matrix having X columns, the second matrix having Y columns and the third matrix having Z columns, wherein X, Y, Z are integers that are equal or greater than 2 and X, Y and Z are each different integers,
   assigning a first color to the first alphanumeric data representation,
   assigning a second color to the second alphanumeric data representation, wherein the first color and the second color are different from each other, and
   visually displaying the first, second and third matrices of colors in a side-by-side relationship.

10. The method according to claim 9, wherein the alphanumeric data is nucleotide sequence data comprising at least 4 different alphanumeric nucleotide representations and at least 4 different colors are assigned to the at least 4 different alphanumeric nucleotide representations.

11. The method according to claim 9, wherein Y equals X+r and Z equals X+2r, wherein r is an integer.

12. The method according to claim 11, wherein the alphanumeric data is nucleotide sequence data comprising at least 4 different alphanumeric nucleotide representations and at least 4 different colors are assigned to the at least 4 different alphanumeric nucleotide representations.

13. The method according to claim 12, wherein the at least 4 different colors are different from a background color against which the at least 4 different colors are displayed.

14. The method according to claim 9, wherein the first and second colors are different from a background color against which the first color and the second color are displayed.

15. The method of expressing at least one characteristic existing in a sequence of symbols $I_1, I_2, \ldots, I_m$, wherein m comprises a positive integer, the method comprising:
   storing the sequence of symbols $I_1, I_2, \ldots, I_m$ in a memory;
   generating parallel sequences A(k) in the form of a matrix X having m matrix elements X(u,v) arranged in n rows and k columns using the sequence of symbols $I_1$, $I_2, \ldots, I_m$ by assigning an element of the sequence of symbols $I_1, I_2, \ldots, I_m$ to each matrix element $X(u,v)$, wherein $X(u,v)=I_j$ and one relationship is satisfied from the group consisting of:

(a) $u=\lceil j \div k \rceil$ and $v=j-(\lceil j \div k \rceil-1) \times k$ for each value of j satisfying $1 \leq j \leq m$, (b) $u=\lceil j \div k \rceil$ and $v=j-(\lceil j \div k \rceil-1) \times k$ for each value of j satisfying $1 \leq j \leq m$ and $\lceil j \div k \rceil$ having a value which comprises an odd integer, and $u=\lceil j \div k \rceil$ and $v=(\lceil j \div k \rceil \times k)-j+1$ for each value of j satisfying $1 \leq j \leq m$ and $\lceil j \div k \rceil$ having a value which comprises an even integer, (c) $u=\lceil j \div k \rceil$ and $v=(\lceil j \div k \rceil \times k)-j+1$ for each value of j satisfying $1 \leq j \leq m$, and (d) $u=\lceil j \div k \rceil$ and $v=(\lceil j \div k \rceil \times k)-j+1$ for each value of j satisfying $1 \leq j \leq m$ and $\lceil j \div k \rceil$ having a value which comprises an odd integer, and $u=\lceil j \div k \rceil$ and $v=j-(\lceil j \div k \rceil-1) \times k$ for each value of j satisfying $1 \leq j \leq m$ and $\lceil j \div k \rceil$ having a value which comprises an even integer, wherein, for each relationship (a)–(d), k comprises an integer satisfying $k \geq 2$, $n=\lceil m \div k \rceil$, $\lceil m \div k \rceil$ comprises the smallest positive integer having a value that is greater than or equal to the value of $m \div k$, and $\lceil j \div k \rceil$ comprises the smallest positive integer having a value that is greater than or equal to the value of $j \div k$;

generating at least three matrices selected from matrices $X_1, X_2, \ldots, X_p$ by further parallel-positioning of parallel sequences $A(p)$, $A(p+r)$, $A(p+2r)$, $A(p+3r)$, . . . converted by changing k to $p, p+r, p+2r, p+3r, \ldots$, wherein p comprises an integer satisfying $p \leq (m \div 2)$, and r comprises an integer; and outputting the at least three matrices using at least one visual expression means selected from the group consisting of a set of squares that are represented by different color hues, color lightness and color saturation, wherein the at least three matrices are visually displayed in a proximal relationship.

16. The method according to claim 15, wherein the sequence of symbols is a nucleotide sequence comprising four different nucleotides and the visual expression means comprises squares represented by four different colors that are representative of the four different nucleotides.

17. The method according to claim 15, further comprising:

(a) extracting symbols sequentially from a sequence of symbols $M_1, M_2, \ldots, M_u$, wherein u comprises a positive integer that will generate the sequence of symbols $I_1, I_2, \ldots, I_m$;

(b) generating the set of parallel sequences $A(k)$ from the extracted sequence of symbols $I_1, I_2, \ldots, I_m$; and repeating steps (a) and (b) while shifting an initiation point within the sequence of symbols $M_1, M_2, \ldots, M_u$ from which the sequence of symbols $I_1, I_2, \ldots, I_m$ is extracted.

18. The method according to claim 17, wherein the sequence of symbols is a nucleotide sequence comprising four different nucleotides and the visual expression means comprises squares represented by four different colors that are representative of the four different nucleotides.

19. The method according to claim 15, further comprising:

sequentially removing symbols from a sequence of symbols $L_1, L_2, \ldots, L_t$ at an interval q to form the sequence of symbols $I_1, I_2, \ldots, I_m$, wherein t has a value $\geq (m \times q)$.

20. The method according to claim 19, wherein the sequence of symbols is a nucleotide sequence comprising four different nucleotides and the visual expression means comprises squares represented by four different colors that are representative of the four different nucleotides.

21. The method according to claim 20, wherein the four different colors are different from a background color against which the four different colors are displayed.

22. The method according to claim 15, wherein the visual expression means is different from a background color against which the at least three matrices are displayed.

23. The method of expressing at least one characteristic existing in a sequence of symbols $I_1, I_2, \ldots, I_m$, wherein m comprises a positive integer and the symbols $I_1, I_2, \ldots, I_m$ are depicted using a first set of visual representations, the method comprising:

storing the sequence of symbols $I_1, I_2, \ldots, I_m$ in a memory;

generating a parallel sequence $A(k)$ in the form of a matrix X having m matrix elements $X(u,v)$ arranged in n rows and k columns using the sequence of symbols $I_1, I_2, \ldots, I_m$ by assigning an element of the sequence of symbols $I_1, I_2, \ldots, I_m$ to each matrix element $X(u,v)$, wherein $X(u,v)=I_j$ and one relationship is satisfied from the group consisting of:

(a) $u=\lceil j \div k \rceil$ and $v=j-(\lceil j \div k \rceil-1) \times k$ for each value of j satisfying $1 \leq j \leq m$, (b) $u=\lceil j \div k \rceil$ and $v=j-(\lceil j \div k \rceil-1) \times k$ for each value of j satisfying $1 \leq j \leq m$ and $\lceil j \div k \rceil$ having a value which comprises an odd integer, and $u=\lceil j \div k \rceil$ and $v=(\lceil j \div k \rceil \times k)-j+1$ for each value of j satisfying $1 \leq j \leq m$ and $\lceil j \div k \rceil$ having a value which comprises an even integer, (c) $u=\lceil j \div k \rceil$ and $v=(\lceil j \div k \rceil \times k)-j+1$ for each value of j satisfying $1 \leq j \leq m$, and (d) $u=\lceil j \div k \rceil$ and $v=(\lceil j \div k \rceil \times k)-j+1$ for each value of j satisfying $1 \leq j \leq m$ and $\lceil j \div k \rceil$ having a value which comprises an odd integer, and $u=\lceil j \div k \rceil$ and $v=j-(\lceil j \div k \rceil-1) \times k$ for each value of j satisfying $1 \leq j \leq m$ and $\lceil j \div k \rceil$ having a value which comprises an even integer, wherein, for each relationship (a)–(d), k comprises an integer satisfying $k \geq 2$, $n=\lceil m \div k \rceil$, $\lceil m \div k \rceil$ comprises the smallest positive integer having a value that is greater than or equal to the value of $m \div k$ and $\lceil j \div k \rceil$ comprises the smallest positive integer having a value that is greater than or equal to the value of $j \div k$;

generating at least three matrices selected from matrices $X_1, X_2, \ldots, X_p$ by further parallel-positioning of parallel sequences $A(p)$, $A(p+r)$, $A(p+2r)$, $A(p+3r)$, . . . converted by changing k to $p, p+r, p+2r, p+3r, \ldots$, wherein p comprises an integer satisfying $p \leq (m \div 2)$, and r comprises an integer;

converting the symbols $I_1, I_2, \ldots, I_m$ to a second set of visual representations $S_1, S_2, \ldots S_m$, the second set of visual representations differing from the first set of visual representations and comprising a plurality of different colors, color hues, color lightness or color saturation; and visually displaying the at least three matrices $X_1, X_2, \ldots, X_p$ of symbols $S_1, S_2, \ldots, S_m$.

24. The method according to claim 23, further comprising:

sequentially removing symbols from a sequence of symbols $L_1, L_2, \ldots, L_t$ at an interval q to form the sequence of symbols $I_1, I_2, \ldots, I_m$, wherein t has a value $\geq (m \times q)$.

25. The method according to claim 23, wherein the sequence of symbols is a nucleotide sequence comprising four different nucleotides and the second set of visual representations comprises squares represented by four different colors that correspond to the four different nucleotides.

26. The method according to claim 23, wherein the at least three matrices of symbols $S_1, S_2, \ldots, S_m$ are visually displayed in a side-by-side relationship.

27. The method according to claim 26, wherein the sequence of symbols is a nucleotide sequence comprising four different nucleotides and the second set of visual representations comprises squares represented by four different colors that correspond to the four different nucleotides.

28. The method according to claim 23, further comprising:

(a) extracting symbols sequentially from a sequence of symbols $M_1, M_2, \ldots, M_u$, wherein u comprises a positive integer that will generate the sequence of symbols $I_1, I_2, \ldots, I_m$;

(b) generating the set of parallel sequences A(k) from the extracted sequence of symbols $I_1, I_2, \ldots, I_m$; and repeating steps (a) and (b) while shifting an initiation point within the sequence of symbols $M_1, M_2, \ldots, M_u$ from which the sequence of symbols $I_1, I_2, \ldots, I_m$ is extracted.

29. The method according to claim 28, wherein the sequence of symbols is a nucleotide sequence comprising four different nucleotides and the second set of visual representations comprises squares represented by four different colors that correspond to the four different nucleotides.

30. The method according to claim 29, wherein the four different colors are different from a background color against which the four different colors are displayed.

31. The method as in claim 23, wherein the symbols $S_1, S_2, \ldots, S_m$ comprise at least two colors that are different from a background color against which the symbols $S_1, S_2, \ldots, S_m$ are displayed.

* * * * *